(12) United States Patent
Wang et al.

(10) Patent No.: US 9,709,506 B2
(45) Date of Patent: Jul. 18, 2017

(54) SUBSTRATE DAMAGE INSPECTION APPARATUS, PRODUCTION SYSTEM AND INSPECTION METHOD

(71) Applicants: BOE TECHNOLOGY GROUP CO., LTD., Beijing (CN); HEFEI BOE OPTOELECTRONICS TECHNOLOGY CO., LTD., Anhui (CN)

(72) Inventors: Zhiqiang Wang, Beijing (CN); Bin Wu, Beijing (CN); Guangzhi Li, Beijing (CN); Xing Yue, Beijing (CN); Xuequan Yu, Beijing (CN); Jiajia Liu, Beijing (CN)

(73) Assignees: BOE TECHNOLOGY GROUP CO., LTD., Beijing (CN); HEFEI BOE OPTOELECTRONICS TECHNOLOGY CO., LTD., Hefei, Anhui (CN)

( * ) Notice: Subject to any disclaimer, the term of this patent is extended or adjusted under 35 U.S.C. 154(b) by 0 days.

(21) Appl. No.: 14/912,577

(22) PCT Filed: Aug. 11, 2015

(86) PCT No.: PCT/CN2015/086624
§ 371 (c)(1),
(2) Date: Feb. 17, 2016

(87) PCT Pub. No.: WO2016/141671
PCT Pub. Date: Sep. 15, 2016

(65) Prior Publication Data
US 2017/0038306 A1    Feb. 9, 2017

(30) Foreign Application Priority Data
Mar. 6, 2015   (CN) .......................... 2015 1 0100199

(51) Int. Cl.
*G01N 21/00* (2006.01)
*G01N 21/88* (2006.01)
(Continued)

(52) U.S. Cl.
CPC ............. *G01N 21/88* (2013.01); *G01N 21/55* (2013.01); *H01L 21/67288* (2013.01); *G01N 2201/088* (2013.01)

(58) Field of Classification Search
CPC .. G01N 21/88; G01N 21/55; G01N 2201/088; H01L 21/67288
(Continued)

(56) References Cited

U.S. PATENT DOCUMENTS

2004/0142642 A1* 7/2004 Thepot .................... B24B 9/148
                                                                     451/43
2006/0082744 A1* 4/2006 Hirukawa ........... G03F 7/70258
                                                                     355/30
2007/0003259 A1    1/2007 Kaihori

FOREIGN PATENT DOCUMENTS

CN         1537227 A      10/2004
CN        101026115        8/2007
(Continued)

OTHER PUBLICATIONS

International Search Report and Written Opinion with English Language Translation, dated Nov. 25, 2015, Application No. PCT/CN2015/086624.
(Continued)

*Primary Examiner* — Sunghee Y Gray
(74) *Attorney, Agent, or Firm* — Blakely Sokoloff Taylor & Zafman LLP

(57) ABSTRACT

The present invention relates to the technical field of display, and particularly relates to a substrate damage inspection apparatus, a production system and an inspection method.
(Continued)

The substrate damage inspection apparatus comprises a drive unit, support rods, sensors and a controller, wherein the drive unit is connected with the support rods so as to drive the support rods to ascend or descend below a substrate to be detected; and the sensors are disposed on the support rods and communicatively connect with the controller, so as to emit light beams to the substrate to be detected, receive the light beams reflected by the substrate to be detected, and feed them back to the controller. By means of the drive unit and the support rods with the sensors, the substrate damage inspection apparatus realizes damage inspection for the substrate to be detected in a vertical direction. That is, a technical solution provided by the present invention allows for damage inspection for the substrate to be detected when it vertically moves. In addition, the substrate damage inspection apparatus is simple in structure and convenient to operate, thereby having strong utility value and significance of generalization.

16 Claims, 2 Drawing Sheets

(51) Int. Cl.
 *G01N 21/55* (2014.01)
 *H01L 21/67* (2006.01)

(58) Field of Classification Search
 USPC .................................................. 356/237.2
 See application file for complete search history.

(56) References Cited

FOREIGN PATENT DOCUMENTS

| | | |
|---|---|---|
| CN | 101026115 A | 8/2007 |
| CN | 201078752 | 6/2008 |
| CN | 101900689 | 12/2010 |
| CN | 102252610 A | 11/2011 |
| CN | 203259481 U | 10/2013 |
| CN | 203396719 | 1/2014 |
| CN | 103792197 A | 5/2014 |
| CN | 104655645 | 5/2015 |
| JP | 2002148196 A | 5/2002 |
| JP | 2007333662 | 12/2007 |
| WO | WO 03/044507 A1 | 5/2003 |

OTHER PUBLICATIONS

Yu et al. "Research on New Method of Glass-Defect Detection." North University of China, Taiyuan, China (Aug. 27, 2008).
Office Action in Chinese Application No. 201510100199.X dated Oct. 9, 2016, with English translation. 9 pages.

\* cited by examiner

SUBSTRATE DAMAGE INSPECTION APPARATUS, PRODUCTION SYSTEM AND INSPECTION METHOD

RELATED APPLICATIONS

The present application is the U.S. national phase entry of PCT/CN2015/086624, with an international filling date of Aug. 11, 2015, which claims the benefit to Chinese Patent Application No. 201510100199.X, filed on Mar. 6, 2015, the entire disclosures of which are incorporated herein by reference.

TECHNICAL FIELD

The present invention relates to the technical field of display, and particularly relates to a substrate damage inspection apparatus, a production system and an inspection method.

BACKGROUND ART

Since entering the 21st century, humanity has progressed into the information automation age, and as an important part in a display element, Thin Film Transistor (TFT) is rapidly developed in visual fields such as a mobile phone and a television.

At present, in an industry of Thin Film Transistor-Liquid Crystal Display (TFT-LCD) and Active Matrix-Organic Light Emitting Diode (AM-OLED), a raw material for making a panel is a glass substrate with a thickness of about 0.3-0.7 mm, and its area may reach $2000\times2500$ mm$^2$. Such a large, thin and crisp glass substrate is very easy to damage in actual production. Once the glass substrate is damaged, glass fragments will greatly affect a production device which has high requirements in both automation and cleanliness. Meanwhile, the glass substrate needs to be treated for a relatively long time after damage, especially for some important devices, for example a coating machine and an exposure machine. Therefore, screening glass substrate damage on an automatic production line is particularly important.

Substrate damage inspection technologies known in the prior art mostly support inspection for an edge of the substrate, which mainly include the three types as follows.

The first one is of image analysis type. That is, in a flowing process of substrate, continuously photographing the substrate, and then analyzing the image, thereby determining whether an edge of the substrate has a defect. A disadvantage of this solution is that an inspection range is limited, only the edge may be inspected, and the substrate can not be completely inspected. Moreover, when the substrate is insufficiently clean, false perception is easily caused in this solution, thereby leading to an incorrect inspection result.

The second one is of optical fiber sensor detection type. That is, respectively installing a reflection type optical fiber sensor at two sides of a device. When the substrate flows through, based on the amount of light received by a receiving end, detect substrate damage on straight lines at two sides. A disadvantage of this solution is that there is a relatively high limitation to an installing position, which makes it difficult to detect a condition of the substrate when transmitting on a manipulator; the detection belongs to a linear type, resulting in a limited detection range; meanwhile, false perception is easily caused when the substrate actually cooperates with a control unit, thus leading to a low reliability.

The third one is of a full-scale type. That is, substrate damage is inspected with regional type detection. However, full-scale inspection is only performed on the substrate damage when the substrate flows horizontally. A disadvantage of this solution is that it is only suitable for inspection when the substrate moves in a horizontal direction. For a case where the substrate moves in a vertical direction, a defect of the substrate can not be detected.

In an implementation of the above prior art, the first two types have been applied in actual production and used in a device before a primary process, but the third type has not been applied yet. However, due to many problems in the above prior art, the substrate damage can not be inspected when the substrate moves vertically. That is, the glass substrate damage can not be detected in a vertical direction.

Therefore, to address the above deficiencies, there is a need for a substrate damage inspection apparatus capable of realizing a substrate damage inspection in a vertical direction, a production system and an inspection method.

SUMMARY OF THE INVENTION (I) Technical Problem to be Solved

An objective of the present invention is to solve a problem such as inspection difficulty for a substrate damage in a vertical direction in the prior art.

(II) Technical Solution

To solve the above technical problem, the present invention provides a substrate damage inspection apparatus, which comprises a drive unit, support rods, sensors and a controller. The drive unit is connected with the support rods for driving the support rods to ascend or descend below a substrate to be detected. The sensors are disposed on the support rods and communicatively connect with the controller, so as to emit light beams to the substrate to be detected, receive the light beams reflected by the substrate to be detected, and feed them back to the controller.

According to an embodiment of the present invention, the support rods are plural in number and are evenly distributed below the substrate to be detected.

According to an embodiment of the present invention, the support rods are distributed in a matrix manner, and each support rod is perpendicular to the substrate to be detected.

According to an embodiment of the present invention, a top end face of each support rod is spaced at the same distance from a bottom surface of the substrate to be detected.

According to an embodiment of the present invention, the sensors are reflection type optical fiber sensors and communicatively connect with the controller through cables.

According to an embodiment of the present invention, the support rods are provided with cavities, and the sensors are embedded in the cavities.

According to an embodiment of the present invention, the drive unit comprises a motor and a drive linkage, wherein the motor is connected to bottom ends of the support rods through the drive linkage, so as to drive the support rods to ascend or descend below the substrate to be detected.

The present invention further provides a production system, which comprises a base platform and the substrate damage inspection apparatus. The substrate damage inspection apparatus is located below the base platform, the base platform is configured to hold the substrate to be detected, and perforation holes allowing passage of the support rods are provided in the base platform.

According to an embodiment of the present invention, the production system further comprises a manipulator. The manipulator is located at one side of the base platform so as to pick or place the substrate to be detected.

In addition, the present invention further provides an inspection method using the substrate damage inspection apparatus, which comprises the following steps:

S1, disposing support rods below a substrate to be detected;

S2, driving the support rods to ascend by a drive unit so as to contact a bottom surface of the substrate to be detected;

S3, during an ascending process of the support rods, emitting light beams to the substrate to be detected by sensors, receiving the light beams reflected by the substrate to be detected, and feeding them back to a controller; and S4, making the following determination by means of the controller according to the light beam information fed back by the sensors:

if the amount of light in the fed light beams present a variation trend of gradually increasing to a constant value, it is determined that the substrate to be detected is not damaged; and if the amount of light in the fed light beams are always close to 0, it is determined that the substrate to be detected is damaged.

(III) Advantageous Effect

The above technical solution of the present invention has advantageous effects as recited below. In the substrate damage inspection apparatus provided by the present invention, the support rods are driven by the drive unit to ascend or descend below the substrate to be detected. Moreover, the sensors capable of emitting light beams to the substrate to be detected, receiving the light beams reflected by the substrate to be detected and feeding them back to the controller are disposed on the support rods, damage inspection for the substrate to be detected in a vertical direction is realized. That is, the technical solution provided by the present invention allows for damage inspection for the substrate to be detected when it vertically moves. In addition, the substrate damage inspection apparatus is simple in structure and convenient to operate, thereby having strong utility value and significance of generalization.

LIST OF REFERENCE NUMBERS

Figure 1:
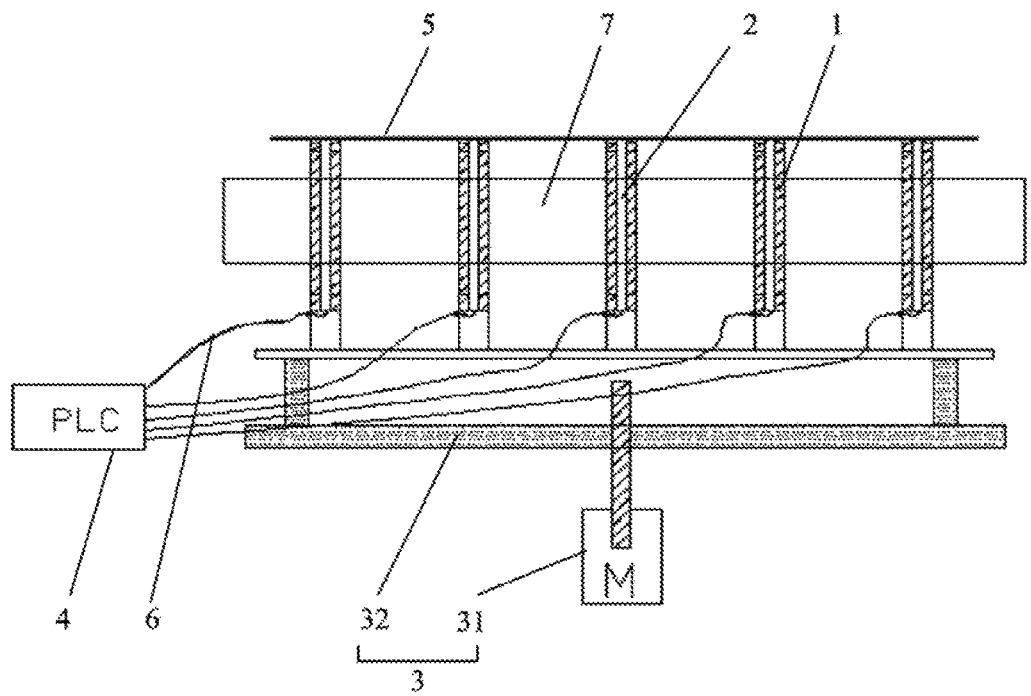
FIG. 1 is a schematic structural view of a substrate damage inspection apparatus according to an embodiment of the present invention.

1: support rod
2: sensor
3: drive unit
4: controller
5: substrate to be detected
6: cable
7: base platform
8: manipulator
21: motor
32: drive linkage.

DETAILED DESCRIPTION OF THE INVENTION

The detailed description of the present invention will be further explained below in detail in connection with drawings and embodiments. The following embodiments are intended to illustrate the present invention, but not to limit a scope of the present invention.

It is noted that in the description of the present invention, the term "plurality" refers to two or more than two, unless otherwise indicated. A directional or positional relationship indicated by terms such as "upper", "lower", "left", "right", "inner", "outer", "front end", "rear end", "head", "tail" and the like is a directional or positional relationship indicated based on the drawings, which is merely intended to describe the present invention and simplify the description, and not intended to indicate or suggest that the indicated apparatus or element must have a specific direction and is constructed or operated in the specific direction, and thus should not to be construed as limiting the present invention. In addition, terms such as "first", "second", "third" and the like are used in a descriptive sense only, and are not intended to indicate or imply relative importance or significance.

It is also noted that in the description of the present invention, terms such as "install", "couple", "connect" and the like should be broadly understood, unless otherwise specifically defined. For example, it may be a fixed connection, a detachable connection, or an integrated connection. In addition, it may be a direct connection, or an indirect connection through an intermediate medium. Those ordinarily skilled in the art may understand specific meaning of the above terms in the present invention depending upon specific conditions.

As shown in FIG. 1, a substrate damage inspection apparatus provided by the present invention comprises a drive unit 3, support rods 1, sensors 2 and a controller 4. The drive unit 3 is connected with the support rods 1 so as to drive the support rods 1 to ascend or descend below a substrate to be detected 5, thereby jacking the substrate to be detected 5. The sensors 2 are disposed on the support rods 1 and communicatively connect with the controller 4, so as to emit light beams to the substrate to be detected 5, receive the light beams reflected by the substrate to be detected 5, and feed them back to the controller 4. Whether the substrate to be detected 5 is damaged or not is determined by analyzing a variation trend of the amount of light, thereby realizing damage inspection for the substrate to be detected in a vertical direction. In this case, both damages caused before the substrate to be detected is jacked and after the substrate to be detected is jacked are considered.

The number of the support rods 1 in this embodiment is not limited to a certain specific number, and may be flexibly changed according to an actual demand. For example, the number of the support rods may be one or plural. When the number of the support rods 1 is plural, the plurality of support rods may be evenly distributed below the substrate to be detected 5 in a scatter-point form, thereby realizing full-scale inspection. In addition, the substrate damage inspection apparatus may perform damage inspection on the substrate to be detected 5 made of a glass material, and also be suitable for a substrate made of other materials.

Figure 2:
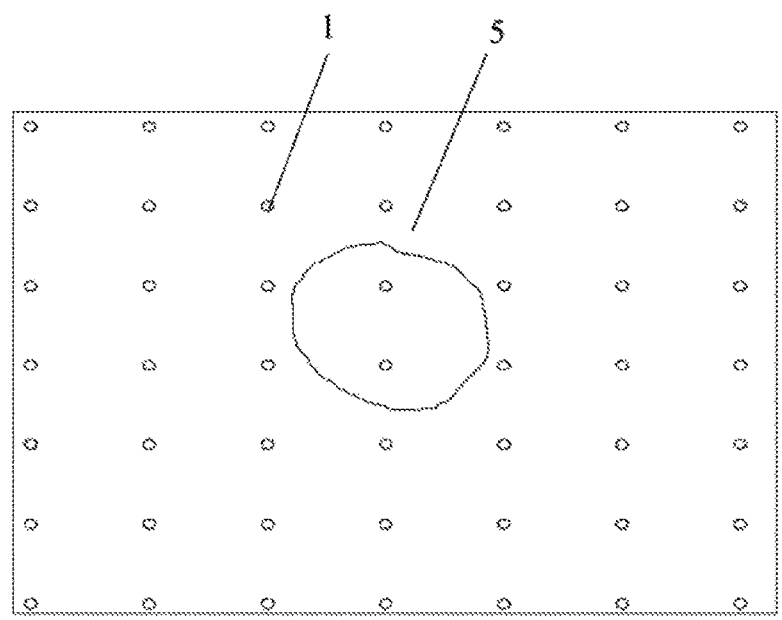
FIG. 2 is a distribution view of support rods below a substrate to be detected according to an embodiment of the present invention.

Further, as shown in FIG. 2, the support rods 1 are distributed in a matrix manner, and each support rod is perpendicular to the substrate to be detected 5. The so-called matrix type distribution is to enable the support rods to be evenly arranged in rows horizontally and in lines longitudinally on the same plane, thereby achieving a scatter-point type uniform inspection on the substrate to be detected 5 in an omni-directional manner. Without doubt, distances between respective support rods 1 may be flexibly changed according to a size of the substrate to be detected 5.

Moreover, in order to make all support rods 1 capable of contacting a bottom surface of the substrate to be detected 5 to achieve a purpose of simultaneously jacking the substrate to be detected 5, and to ensure a detection accuracy, distances between top end faces of the support rods 1 and the bottom surface of the substrate to be detected 5 are set to be equal. Without doubt, for the sake of compact and attractive structure, length of each support rod should be equal.

The sensors in this embodiment may alternatively be reflection type optical fiber sensors, and communicatively connect with the controller 4 through cables 6.

According to an embodiment of the present invention, the reflection type optical fiber sensor is provided with a light source and a light receiving apparatus, wherein a light beam emitted from the light source is received by a photosensitive element after reflected by an object to be detected, and then fed back to the controller 4 after processed by a control circuit. The controller 4 may be a programmable logic controller (PLC), which employs one kind of programmable memory to store programs therein and execute user-oriented instructions such as logical operation, sequential control, timing, counting and arithmetical operation. By setting a threshold for the amount of light and a time for detection (including starting time and ending time), detection on an imperfect raw material of the substrate may be realized. Moreover, a detection result is displayed in real time by a digital or analog type input/output.

Moreover, the sensors 2 may be embedded on the support rods 1, such that the structure is hidden without causing interference to other devices. Correspondingly, cavities configured to hold the sensors 2 are disposed on the support rods 1. The sensors 2 are embedded in the cavities, and the front end faces of the sensors 2 are remained parallel to the bottom surface of the substrate to be detected 5, thereby improving conversion efficiency when the light beams are reflected.

In addition, the drive unit 3 in this embodiment comprises a motor 31 and a drive linkage 32, wherein the motor 31 is connected to bottom ends of the support rods 1 so as to drive the support rods 1 to ascend or descend below the substrate to be detected 5. In addition, the drive linkage 32 has a function for converting a rotary movement of the motor 31 into a linear movement, which may employ a screw drive mechanism in actual production. Briefly, the drive linkage 32 is a ball screw mechanism, wherein a screw rod thereof is connected with the motor 31, a screw nut thereof is thread-connected with the screw rod, and a plurality of support rods 1 are connected with the screw nut through a connecting plate. When the motor 31 rotates, the screw nut may ascend or descend in a vertical direction, thereby driving the support rods 1 to ascend or descend simultaneously. Such a structure is simple and has high degree of automation.

Figure 3:
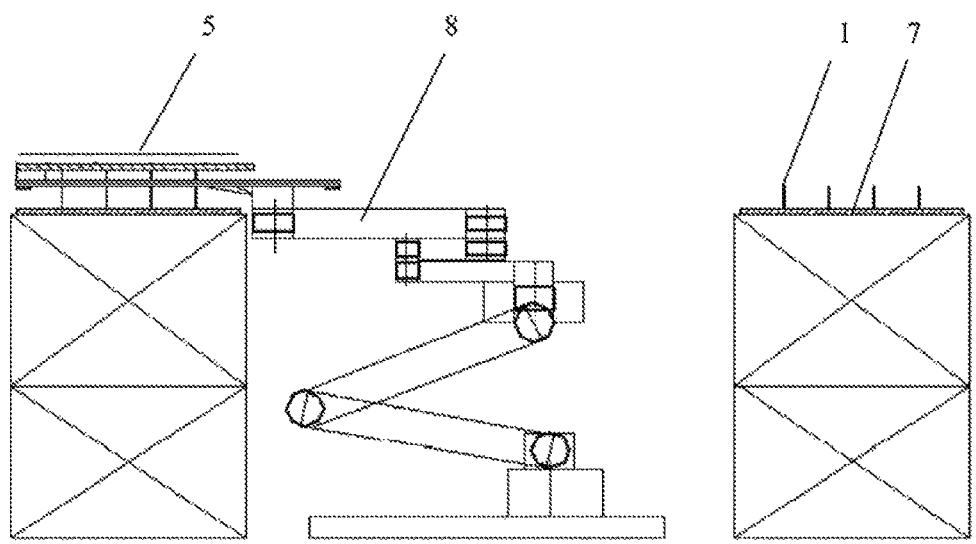
FIG. 3 is a schematic structural view of a production system according to an embodiment of the present invention.

As shown in FIG. 3, the present invention further provides a production system, which comprises a base platform 7 and the substrate damage inspection apparatus as describe above. The substrate damage inspection apparatus is located below the base platform 7. Particularly the plurality of support rods 1 may be evenly distributed below the base platform 7 in a scatter-point form. The base platform 7 is configured to hold the substrate to be detected 5, and perforation holes allowing passage of the support rods 1 are provided in the base platform 7. Particularly, the support rods 1 may pass through the perforation holes when ascending so as to finally jack the substrate to be detected 5.

The production system further comprises a manipulator 8, wherein the manipulator 8 is located at one side of the base platform 7 to pick or place the substrate to be detected 5. For example, when the substrate to be detected 5 is jacked, the manipulator 8 may convey the substrate to be detected 5 from upstream of the base platform 7 to downstream of the base platform 7. The manipulator 8 is convenient to operate and has high degree of automation.

In addition, the present invention further provides an inspection method using the substrate damage inspection apparatus, which comprises the steps as follows.

S1, disposing support rods below a substrate to be detected specifically, firstly placing the substrate to be detected on a base platform, and evenly distributing a plurality of support rods below the base platform, each support rod being perpendicular to the substrate to be detected and spaced at the same distance from the substrate to be detected.

S2, driving the support rods to ascend by a drive unit so as to contact the substrate to be detected specifically, starting the motor to enable the support rods to ascend along a vertical direction under the drive of a drive linkage, so that the support rods may jack the substrate to be detected after passing through perforation holes.

S3, during an ascending process of the support rods, emitting light beams to the substrate to be detected by sensors, receiving the light beams reflected by the substrate to be detected, and feeding them back to a controller specifically, the sensors have functions for emitting and receiving light beams and determining on the amount of light in the light beams, thus being in a normally-opened state in production.

S4, making the following determination by means of the controller according to the light beam information fed back by the sensors:

if the amount of light in the fed light beams present a variation trend of gradually increasing to a constant value, it is determined that the substrate to be detected is not damaged. Specifically, when the support rods ascend at a constant speed, the amount of light linearly increase and reach a constant value. The reason for this is that during the ascending process of the support rods, the amount of light in the received light beams linearly gradually increase, and when the support rods ascend to positions contacting the substrate to be detected, the amount of light received by the sensors may reach a constant value F. When the substrate to be detected is complete, the amount of light finally received by the optical fiber sensors is that constant value F.

In addition, if the amount of light in the fed light beams is always close to 0 (far smaller than the constant value F), it is determined that the substrate to be detected is damaged. Specifically, when the substrate to be detected is damaged before ascending or during the ascending process (a middle position of the substrate to be detected as in FIG. 2), the amount of light received by the support rods below a position where the damage is located are all 0. In this way, the PLC receives a signal, which is smaller than the amount of light reflected by a normal substrate. With analysis and output of alarm information, inspection for the damaged glass is completed. After the substrate to be detected is jacked, it is conveyed to downstream of the base platform by the manipulator. At this moment, the amount of light received by all sensors is returned to 0, thereby ending a detection process.

Accordingly, the present invention provides a substrate damage inspection apparatus, wherein the support rods are driven by the drive unit so as to ascend or descend below the substrate to be detected, and the sensors capable of emitting light beams to the substrate to be detected, receiving the light beams reflected by the substrate to be detected and feeding them back to the controller are disposed on the support rods, so that damage inspection for the substrate to be detected in a vertical direction is realized. That is, a technical solution provided by the present invention allows for damage inspection for the substrate to be detected when it vertically moves. In addition, the substrate damage inspection apparatus is simple in structure and convenient to operate, thereby having strong utility value and significance of generalization.

Embodiments of the present invention have been presented only for the purpose of illustration and description and are not intended to be exhaustive or to limit the present invention to those forms as disclosed. Many modifications and variations will be apparent to those ordinarily skilled in the art. The embodiments were chosen and described in order to best explain principles and practical application of the present invention, and to enable others ordinarily skilled in the art to understand the present invention so as to contemplate various embodiments with various modifications as suited to the particular use.

The invention claimed is:

1. A substrate damage inspection apparatus, comprising a drive unit, support rods, sensors and a controller, wherein
said drive unit is connected with said support rods so as to drive said support rods to ascend or descend below a substrate to be detected; and
said sensors are disposed inside said support rods and communicatively connect with said controller, so as to emit light beams to the substrate to be detected, receive light beams reflected by the substrate to be detected, and feed them back to said controller.

2. The substrate damage inspection apparatus according to claim 1, wherein said support rods are plural in number and are evenly distributed below the substrate to be detected.

3. The substrate damage inspection apparatus according to claim 2, wherein said support rods are distributed in a matrix manner and each support rod is perpendicular to the substrate to be detected.

4. The substrate damage inspection apparatus according to claim 2, wherein a top end face of each support rods is spaced at the same distance from a bottom surface of the substrate to be detected.

5. The substrate damage inspection apparatus according to claim 1, wherein said sensors are reflection type optical fiber sensors and communicatively connect with said controller through cables.

6. The substrate damage inspection apparatus according to claim 5, wherein said support rods are provided with cavities, and said sensors are embedded in said cavities.

7. The substrate damage inspection apparatus according to claim 1, wherein said drive unit comprises a motor and a drive linkage, wherein said motor is connected to a bottom end of said support rod through said drive linkage, so as to drive said support rods to ascend or descend below the substrate to be detected.

8. A production system, comprising a base platform and the substrate damage inspection apparatus according to claim 1, wherein
said substrate damage inspection apparatus is located below said base platform, said base platform is configured to hold the substrate to be detected, and perforation holes allowing passage of said support rods are provided in said base platform.

9. The production system according to claim 8, further comprising a manipulator, wherein said manipulator is located at one side of said base platform so as to pick or place the substrate to be detected.

10. An inspection method using the substrate damage inspection apparatus according to claim 1, comprising the following steps:
S1, disposing support rods below the substrate to be detected;
S2, driving the support rods to ascend by a drive unit so as to contact the substrate to be detected;
S3, during an ascending process of said support rods, emitting light beams to the substrate to be detected by sensors, receiving light beams reflected by the substrate to be detected, and feeding them back to a controller; and
S4, making the following determination by means of the controller according to the light beam information fed back by the sensors:
if the amount of light in the fed light beams present a variation trend of gradually increasing to a constant value, it is determined that the substrate to be detected is not damaged; and
if the amount of light in the fed light beams are always close to 0, it is determined that the substrate to be detected is damaged.

11. The production system according to claim 8, wherein said support rods are plural in number and are evenly distributed below the substrate to be detected.

12. The production system according to claim 8, wherein said sensors are reflection type optical fiber sensors and communicatively connect with said controller through cables.

13. The production system according to claim 8, wherein said drive unit comprises a motor and a drive linkage, wherein said motor is connected to a bottom end of said support rod through said drive linkage, so as to drive said support rods to ascend or descend below the substrate to be detected.

14. The inspection method according to claim 10, wherein said support rods are plural in number and are evenly distributed below the substrate to be detected.

15. The inspection method according to claim 10, wherein said sensors are reflection type optical fiber sensors and communicatively connect with said controller through cables.

16. The inspection method according to claim 10, wherein said drive unit comprises a motor and a drive linkage, wherein said motor is connected to a bottom end of said support rod through said drive linkage, so as to drive said support rods to ascend or descend below the substrate to be detected.

* * * * *